(12) United States Patent
Lee et al.

(10) Patent No.: US 10,940,479 B2
(45) Date of Patent: Mar. 9, 2021

(54) COLLECTION BOTTLE AND METHOD FOR DETECTING CHARACTERISTIC OF SAMPLE

(71) Applicant: BONRAYBIO CO., LTD., Taichung (TW)

(72) Inventors: Hui-Ying Lee, Changhua County (TW); Cheng-Teng Hsu, Taichung (TW); Yu-Chiao Chi, Taoyuan (TW); Kuang-Li Huang, Taichung (TW)

(73) Assignee: BONRAYBIO CO., LTD., Taichung (TW)

( * ) Notice: Subject to any disclaimer, the term of this patent is extended or adjusted under 35 U.S.C. 154(b) by 252 days.

(21) Appl. No.: 15/586,289

(22) Filed: May 4, 2017

(65) Prior Publication Data

US 2018/0104681 A1    Apr. 19, 2018

(30) Foreign Application Priority Data

Oct. 19, 2016 (TW) .................................. 105133628

(51) Int. Cl.
*B01L 3/00* (2006.01)
*A61B 10/00* (2006.01)
(Continued)

(52) U.S. Cl.
CPC .......... *B01L 3/508* (2013.01); *A61B 10/0058* (2013.01); *A61B 10/0096* (2013.01);
(Continued)

(58) Field of Classification Search
CPC ............ A61B 10/0058; A61B 10/0096; G01N 11/00; G01N 33/487; B01L 2300/028;
(Continued)

(56) References Cited

U.S. PATENT DOCUMENTS

| | | | |
|---|---|---|---|
| 5,524,783 A | 6/1996 | Poppff | |
| 5,944,703 A * | 8/1999 | Dixon | A61M 1/0003 604/319 |

(Continued)

FOREIGN PATENT DOCUMENTS

| | | |
|---|---|---|
| CN | 2711734 | 7/2005 |
| CN | 201867313 | 6/2011 |

(Continued)

OTHER PUBLICATIONS

Software translation of CN201867313 to Shenzhen Gld Bio Tech Co LTD, originally published on Jun. 15, 2011. (Year: 2011).*

(Continued)

*Primary Examiner* — Christopher Adam Hixson
*Assistant Examiner* — Michelle Adams
(74) *Attorney, Agent, or Firm* — JCIPRNET (57) ABSTRACT

A collection bottle and a method for detecting a characteristic of a sample are provided. The collection bottle includes a body and a cover. The body of the collection bottle has an accommodating space. The cover of the collection bottle is removably assembled to the body of the collection bottle, and the cover includes a channel and a testing part. The channel of the collection bottle communicates the accommodating space and the outside environment. While the cover of the collection bottle is assembled to the body, the testing part extends toward the accommodating space.

14 Claims, 10 Drawing Sheets

(51) Int. Cl.
  *G01N 33/487* (2006.01)
  *G01G 19/52* (2006.01)
  *G01N 11/00* (2006.01)
  *G01N 33/52* (2006.01)

(52) U.S. Cl.
  CPC ............... *B01L 3/50* (2013.01); *G01G 19/52* (2013.01); *G01N 11/00* (2013.01); *G01N 33/487* (2013.01); *G01N 33/52* (2013.01); *B01L 2200/14* (2013.01); *B01L 2300/028* (2013.01); *B01L 2300/041* (2013.01); *B01L 2300/042* (2013.01); *B01L 2300/046* (2013.01); *B01L 2300/047* (2013.01); *B01L 2300/0663* (2013.01); *B01L 2300/0825* (2013.01); *B01L 2300/0832* (2013.01); *B01L 2300/0851* (2013.01); *B01L 2300/123* (2013.01)

(58) Field of Classification Search
  CPC .... B01L 2300/0851; B01L 3/50; B01L 3/508; B01L 2300/0832
  See application file for complete search history.

(56) References Cited

U.S. PATENT DOCUMENTS

| | | | | |
|---|---|---|---|---|
| 5,976,895 | A * | 11/1999 | Cipkowski | A61B 10/007 422/412 |
| 6,627,152 | B1 * | 9/2003 | Wong | A61B 10/0045 422/408 |
| 7,198,167 | B2 * | 4/2007 | Marsden | A47G 19/2272 206/538 |
| D842,494 | S * | 3/2019 | Lee | D24/224 |
| 2004/0147036 | A1 | 7/2004 | Krenn et al. | |

FOREIGN PATENT DOCUMENTS

| | | |
|---|---|---|
| CN | 203101125 | 7/2013 |
| CN | 203178092 | 9/2013 |
| CN | 203953704 | 11/2014 |
| CN | 204660371 | 9/2015 |
| CN | 205023125 | 2/2016 |
| CN | 105466726 | 4/2016 |
| CN | 205235988 | 5/2016 |
| EP | 3034160 | 6/2016 |
| TW | M458202 | 8/2013 |
| TW | M537208 | 2/2017 |
| WO | 9735512 | 10/1997 |

OTHER PUBLICATIONS

"Approximate, v." OED Online, Oxford University Press, Mar. 2020, www.oed.com/view/Entry/9904. Accessed Mar. 28, 2020. (Year: 2020).*

CN-205023125-U software translation, generated at espacenet.com on Aug. 29, 2020 (Year: 2020).*

"Search Report of Europe Counterpart Application", dated Jan. 23, 2018, p. 1-p. 9, in which the listed references were cited.

"Office Action of Taiwan Counterpart Application," dated Jul. 13, 2017, p. 1-p. 5, in which the listed references were cited.

"Search Report of Europe Counterpart Application", dated Jun. 25, 2019, pp. 1-8.

"Office Action of China Counterpart Application," dated Aug. 14, 2019, p. 1-p. 9.

"Office Action of China Counterpart Application", dated Apr. 24, 2020, pp. 1-8.

* cited by examiner

COLLECTION BOTTLE AND METHOD FOR DETECTING CHARACTERISTIC OF SAMPLE

CROSS-REFERENCE TO RELATED APPLICATION

This application claims the priority benefit of Taiwan application serial no. 105133628, filed on Oct. 19, 2016. The entirety of the above-mentioned patent application is hereby incorporated by reference herein and made a part of this specification.

BACKGROUND OF THE INVENTION

1. Field of the Invention

The invention relates to a collection device and a sample detecting method, and particularly relates to a collection bottle and a method for detecting a characteristic of a sample.

2. Description of Related Art

Regarding conventional sample testing methods, it is common to store a sample in a sample collection bottle. When the test needs to be carried out, the sample is taken out from the collection bottle for analysis. Before analyzing and testing the sample, the cover of the sample collection bottle needs be opened. However, at this step, the smell of the sample may be released from the sample collection bottle, and the sample may even be spilled during the process of opening the cover. For example, currently some medical procedures in the long term testing category carried out at infertility patients include semen testing. This testing category is mainly directed at performing observations on the characteristics of semen, such as the level of liquefaction of semen. The observation on the level of liquefaction of semen is performed by obtaining a suitable amount of semen by using a dropper, and determining the level of liquefaction of semen by observing the length of stringiness of the sample during dripping of the semen.

In addition to the testing category described in the foregoing, there are also needs for observation on other medical samples, aqueous substances, or solid substances etc. Therefore, a collection device allowing observation on the characteristics of the sample without opening the cover is required to cope with such needs.

SUMMARY OF THE INVENTION

The invention provides a collection bottle and a method for detecting a characteristic of a sample that is capable of preventing a smell from spreading out when the sample is being detected, or preventing the sample from being spilled when opening the cover from the collection bottle.

An embodiment of the invention provides a collection bottle. The collection bottle includes a body and a cover. The body has an accommodating space and the cover is removably assembled to the body. The cover includes a channel and a testing part, the channel communicates the accommodating space and an outside environment, and when the cover is assembled to the body, the testing part extends toward the accommodating space.

According to an embodiment of the invention, the testing part is a column-shaped, cone-shaped or cruciform structure. In addition, based on different samples, the testing part may be combined with a test paper or coated with a test reagent, so as to detect the characteristic of the sample.

According to an embodiment of the invention, a slot is disposed to the testing part.

According to an embodiment of the invention, a distance is kept between a bottom part of the testing part and a bottom part of the body. The distance may be in a range from 1 mm to 50 mm, for example, and may also be 20 mm.

According to an embodiment of the invention, the body is provided with a scale.

According to an embodiment of the invention, a material of the body includes an elastic material.

According to an embodiment of the invention, a bottom part of the body has a bulging part.

According to an embodiment of the invention, the collection bottle further includes a shielding cap. The shielding cap is removably assembled to the cover and closes (or sealed) the channel.

According to an embodiment of the invention, the shielding cap has an extended connection band, and an end of the connection band is connected to the cover.

According to an embodiment of the invention, the cover further includes a fixing part located adjacent to the channel, and the shielding cap is configured to be engaged with the fixing part and used to close the channel.

According to an embodiment of the invention, a collected sample is semen.

A method for detecting a characteristic of a sample according to an embodiment is performed by using the collection bottle. The steps of the method includes: after the cover is opened, placing a sample in the accommodating space, then assembling the cover to the body, and having the testing part dipped in the sample by tilting or shaking, so as to determine the characteristic of the sample.

According to an embodiment of the invention, after the sample is placed in the accommodating space, the testing part is made to be dipped in the sample after a incubation period, and a dripping frequency or a length of stringiness of the sample is observed, so as to determine a level of liquefaction of the sample.

According to an embodiment of the invention, after the testing part is made to be dipped in the sample, a test paper or a test reagent disposed on the testing part is observed, so as to detect a characteristic of the sample, such as a pH value of the sample or other characteristics. Based on different samples under test, different test papers may be disposed to or different test reagents may be coated on the testing part.

In view of the foregoing, the collection bottle and the method for detecting the characteristic of the sample according to the embodiments of the invention are able to detect the characteristic of the sample by using the testing part without opening the cover. If the sample needs to be taken out, the sample can be exported via the channel on the cover, so as to prevent the bottle from being completely flipped over.

To make the above features and advantages of the invention more comprehensible, embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
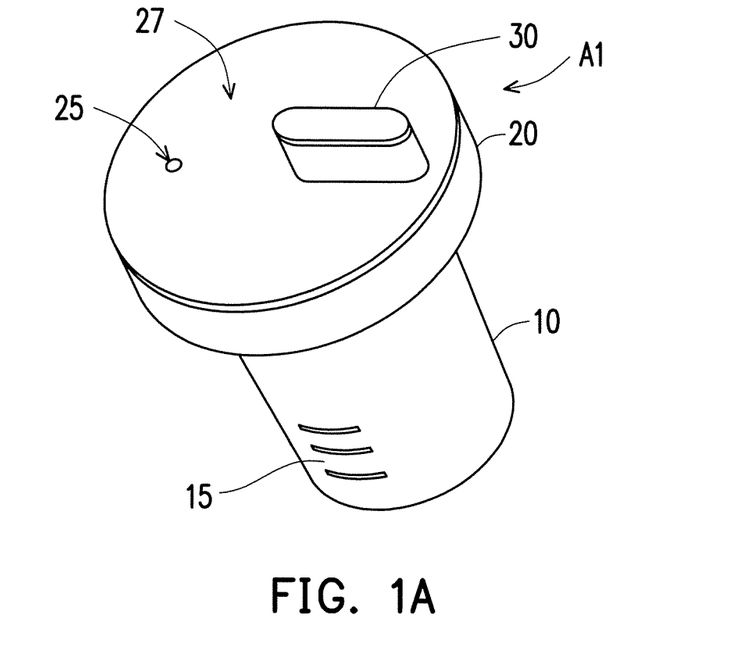
FIG. 1A is a schematic perspective view illustrating a collection bottle according to an embodiment of the disclosure.
Figure 1B:
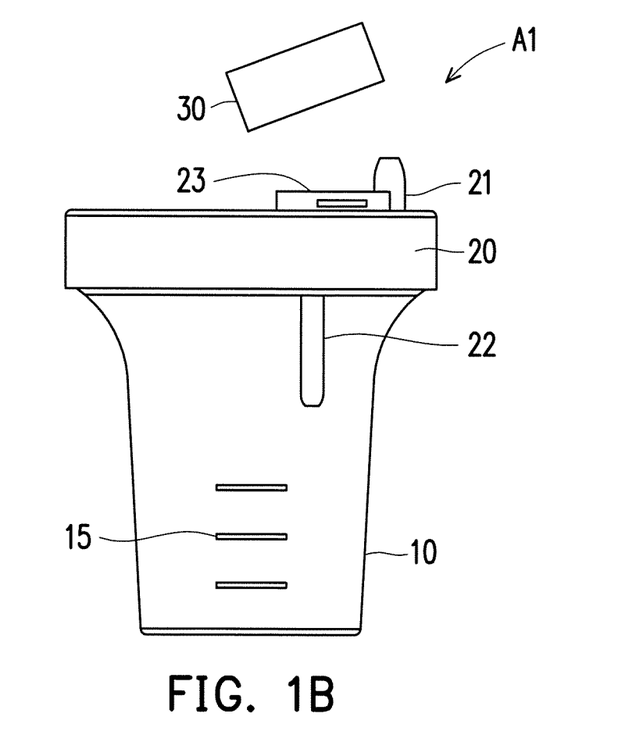
FIG. 1B is a schematic side view illustrating the collection bottle of FIG. 1A.
Figure 1C:
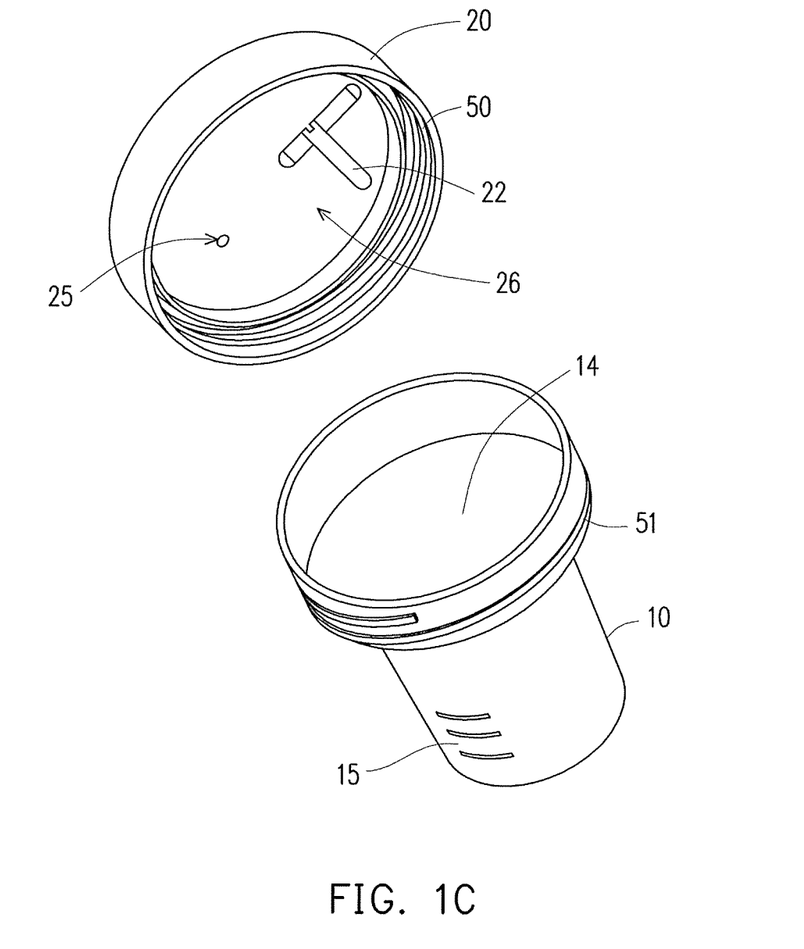
FIG. 1C is a schematic perspective view illustrating that a cover and a body of FIG. 1A are separated.

Reference will now be made in detail to the present preferred embodiments of the invention, examples of which are illustrated in the accompanying drawings. Wherever possible, the same reference numbers are used in the drawings and the description to refer to the same or like parts. FIGS. 1A to 1C illustrate an embodiment of a collection bottle of the invention. However, the embodiment is described herein for an illustrative purpose, and the protection scope of the invention shall not be limited by the embodiment. A collection bottle A1 of the embodiment includes a body 10 and a cover 20. The body 10 has an accommodating space 14, and the cover 20 is removably assembled to the body 10. The cover 20 has a channel 21 and a testing part 22. The channel 21 communicates the accommodating space 14 and an outside environment, and the testing part 22 is disposed to a bottom surface 26 of the cover 20. When the cover 20 is assembled to the body 10, the testing part 22 extends along a direction toward the accommodating space 14, and is preferably disposed along and approximate to the channel. Since the testing part 22 may be configured to be dipped in a sample (not shown) in the body 10, and a test paper may be attached to the testing part 22, or a test reagent may be coated on the testing part 22, the characteristics of sample such as density, viscosity, level of transparency, level of liquefaction, pH value, residual chlorine, rigidity, and the like of the sample can be observed or detected when the testing part 22 is dipped the sample and without taking out the sample from the body 10. Therefore, drawbacks such as deterioration or spilling of the sample, release of the smell, and the like when the sample is taken out can be avoided. Since the cover 20 has the channel 21, the user can take out the sample by opening a shielding cap 30 and tilting the body 10 to let the sample flow through the channel 21. Therefore, the cover 20 does not need to be completely open to take the sample out. A situation of completely spilling the sample when opening the cover 20 can be prevented, and an extent to which the smell is released can be reduced.

The body 10 of the embodiment may be formed of a transparent material or a semi-transparent material. In addition, the body 10 may also be provided with a scale 15. The collection bottle A1 of this embodiment can further include the shielding cap 30. The shielding cap 30 is removably assembled to the cover 20. The testing part 22 of this embodiment is a column-shaped structure, such as a cylindrical shape or an elongated column-shaped structure. Based on colors of different samples, a material in contrast color to the sample can be chosen for the testing part 22. For example, if the sample is white, a contrast color, such as black, can be chosen for the testing part 22 to facilitate observation on a length of stringiness or a dripping frequency of the sample. A top surface 27 of the cover 20 can further include a fixing part 23. The fixing part 23 is disposed to the top surface 27 of the cover 20 and located beside the channel 21. The shielding cap 30 can be engaged with the fixing part 23. When the shielding cap 30 is assembled to the cover 20, the shielding cap 30 closes the channel 21 to prevent the sample in the accommodating space 14 from spilling or leaking. The shielding cap 30 is an annular structure disposed in correspondence with shapes of the fixing part 23 and the channel 21.

As shown in FIGS. 1A and 1B, the shielding cap 30 covers the fixing part 23 and the channel 21 and is assembled to the cover 20. The shielding cap 30 can be stably fixed onto the cover 20 by means of the fixing part 23. The user can observe the scale 15 to obtain a volume of a sample 40 in the accommodating space 14. The scale 15 can further allow the user to test the length of stringiness or the dripping frequency when the sample flows through the testing part 22, so as to evaluate the level of liquefaction, density, or viscosity of the sample. Alternatively, an additional scale (not shown) can be provided on the body 10 for the user to observe an absolute value of the length of stringiness of the sample. The additionally provided scale can also be defined as an indication line to provide a convenient means to determine whether the level of liquefaction, density, or whether the viscosity of the sample is not normal or not. As shown in FIG. 1C, the body 10 and the cover 20 can be combined by means of screw threads. The cover 20 has an internal thread 50, and a top end of the body 10 has an external thread 51. By assembling with the threads, the body 10 is able to be tightly fastened to or separated from the cover 20. It should be noted that, the invention does not intend to limit the way of combining the body and the cover. The accommodating space 14 fulfills the need of some types of the sample 40 that require an incubation period before being tested. For example, before being tested for the level of liquefaction, semen requires an incubation period under room temperature, and the preferably incubation period is 20 to 70 minutes. Under such circumstance, the sample 40 can be placed into the accommodating space 14 of the body 10 and wait for a period of time.

A method for detecting a characteristic of a sample according to the former embodiment can be performed by using the collection bottle A1 or other collection bottles compliant with the principles of the invention. In this embodiment, the method for detecting the characteristic of the sample of the embodiment comprises the following steps. After the cover is opened, the sample is placed in the accommodating space, and then the cover is assembled to the body. The testing part is dipped in the sample by tilting or shaking, so as to determine the characteristic of the sample. In an embodiment, after the testing part is dipped in the sample, the test paper or the test reagent disposed on the testing part is observed to detect the characteristic of the sample. In another embodiment, after the sample is placed in the accommodating space, the testing part is dipped in the sample after the incubation period, and the dripping frequency or the length of stringiness of the sample is observed, so as to determine the level of liquefaction of the sample. Details of the method for detecting the characteristic of the sample are described in the following with reference to the accompanying drawings.

Figure 2A:
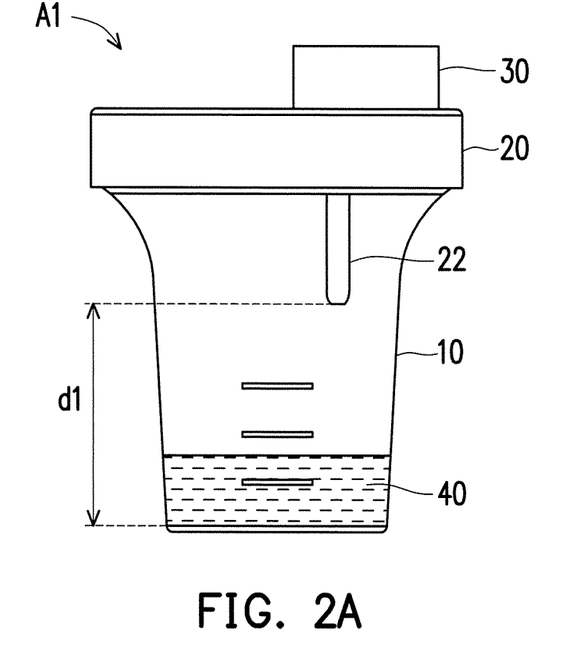
FIGS. 2A to 2E are schematic views illustrating states of use of the collection bottle of FIG. 1A.
Figure 2B:
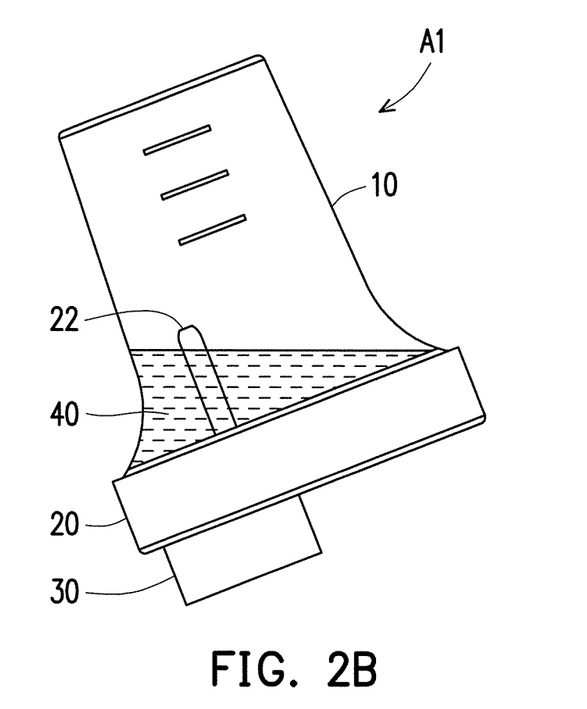
Figure 2C:
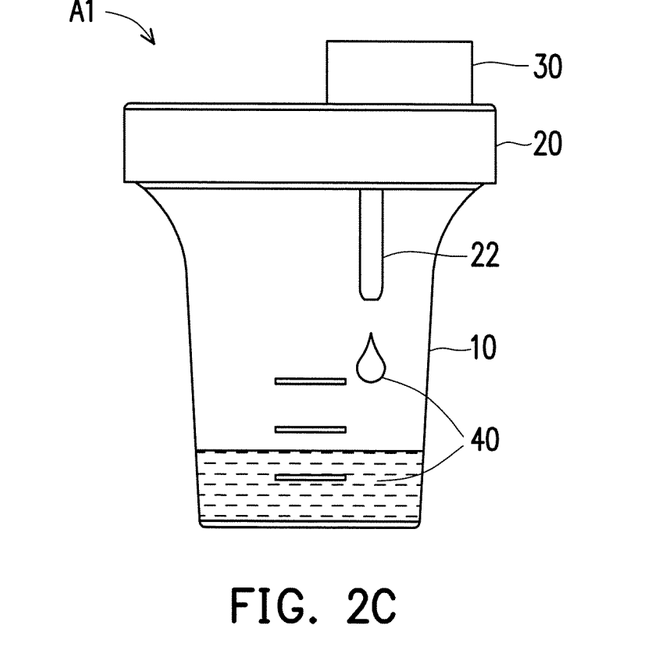

As shown in FIG. 2A, a distance d1 is defined between a bottom part of the testing part 22 and a bottom part of the body 10. The distance d1 is in a range from 1 mm to 50 mm, and preferably is 20 mm. Before conducting a test by using the collection bottle A1, the sample 40 to be tested is placed into the accommodating space 14 (shown in FIG. 1C), and the volume of the sample 40 is observed with reference to the scale 15 of the body 10. Then, as shown in FIG. 2b, the collection bottle A1 is shaken up and down, so that the sample 40 is moved to the bottom surface of the cover 20 and contacts the testing part 22. Then, as shown in FIG. 2C, the user keeps the collection table A1 still and observes the sample 40. Due to the distance d1 between the bottom part of the testing part 22 and the bottom part of the body 10, there is room for the sample 40 to drip from the testing part 22 to the bottom part of the body. Based on dripping of the sample 40, the user can conduct an analysis to obtain the level of liquefaction, density, or viscosity of the sample 40, thereby enabling the user to quickly and conveniently learn the characteristic of the sample. If a length of the testing part 22 is designed such that the bottom part of the testing part 22 is close to the bottom part of the body 10, namely the bottom part of the testing part 22 is anticipated to come into contact with the sample often, the testing part 22 can serve to stir the sample 40.

Figure 2D:
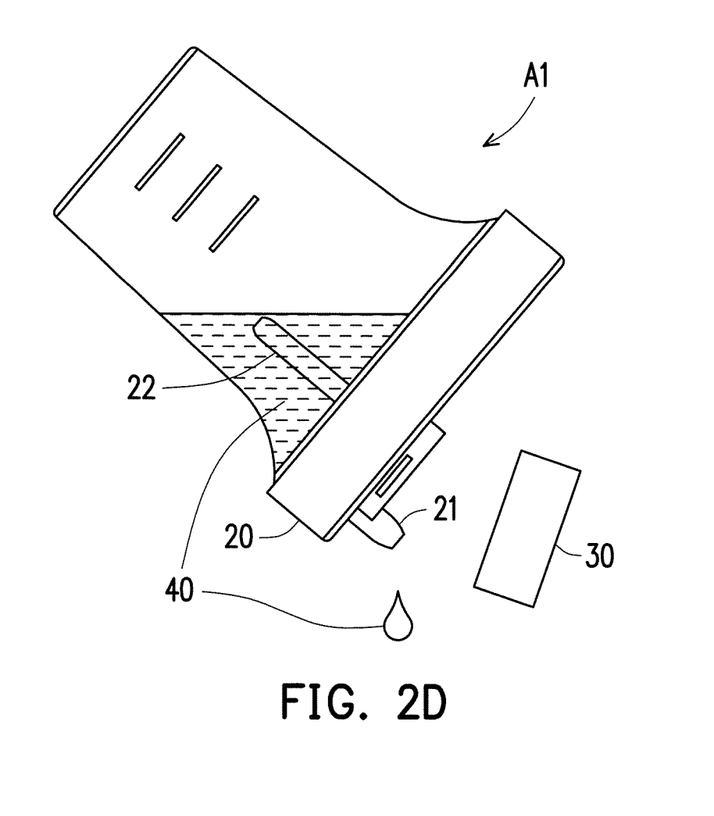
Figure 2E:
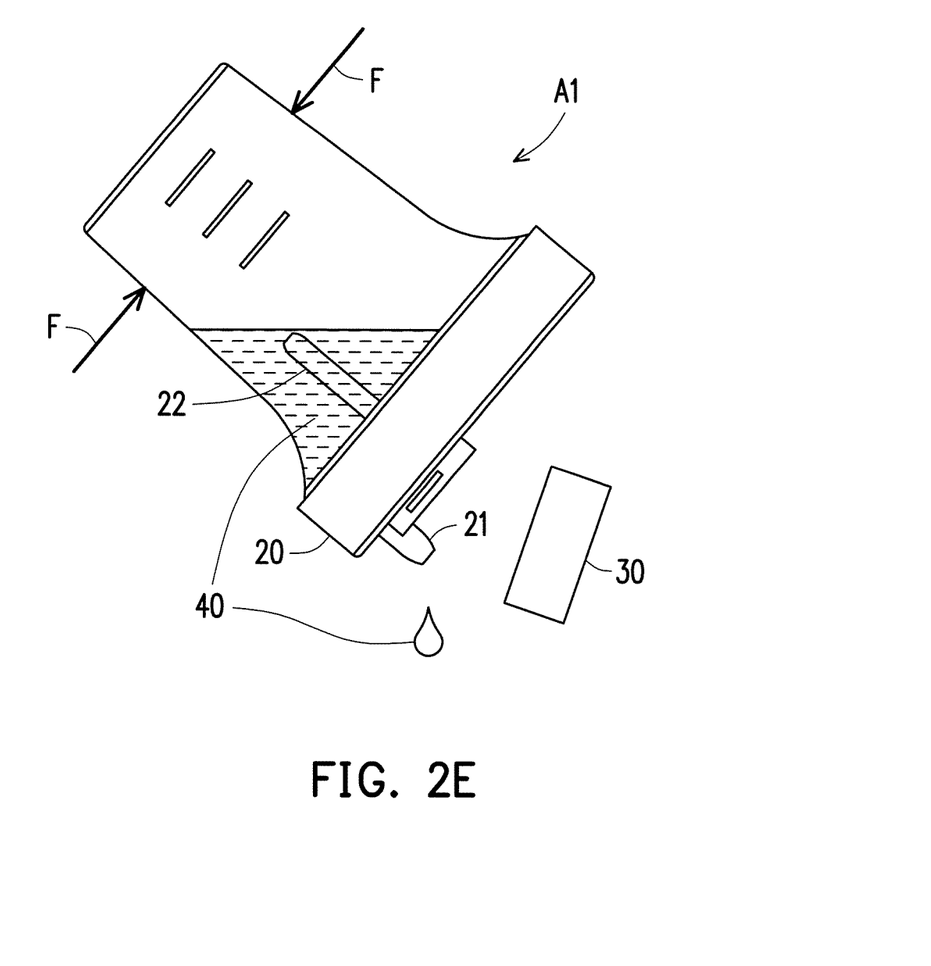

As shown in FIG. 2D, after the shielding cap 30 is removed from the cover 20, the collection bottle A1 is tilted, so the sample 40 can be outputted from the accommodating space of the collection bottle A1 14 via the channel 21, and drop spontaneously in accordance with a direction of gravity for subsequent testing, such as high-resolution magnifying observation on the sample 40. Considering the smoothness of the spontaneous dropping of the sample 40, a ventilating hole 25 (shown in FIG. 1A) can be additionally disposed on the cover 20, so that the space in the body 10 is in communication with the outside environment. Moreover, as shown in FIG. 2E, when an elastic material is chosen as the material of the body 10, an external force F can be applied to the body 10, so that the sample 40 can be squeezed and exported out of the collection bottle A1 via the channel 21. Accordingly, in this embodiment, the user is able to obtain testing records of the sample 40 without opening the cover 20 when the user conducts a test by using the collection bottle A1. If the sample 40 needs to be taken out for testing, the sample 40 can be taken out via the channel 21 on the cover 20. The collection bottle A1 is able to effectively prevent the smell of the sample 40 from being released or prevent the sample 40 from being flipped over and spilled. Also, when the collection bottle A1 is tiled and the sample 40 is exported out of the collection bottle A1 from the accommodating space 14 via the channel 21, the sample 40 also flows through the testing part 20. When the collection bottle A1 is placed upright, the dripping of the sample 40 can still be observed.

Figure 3A:
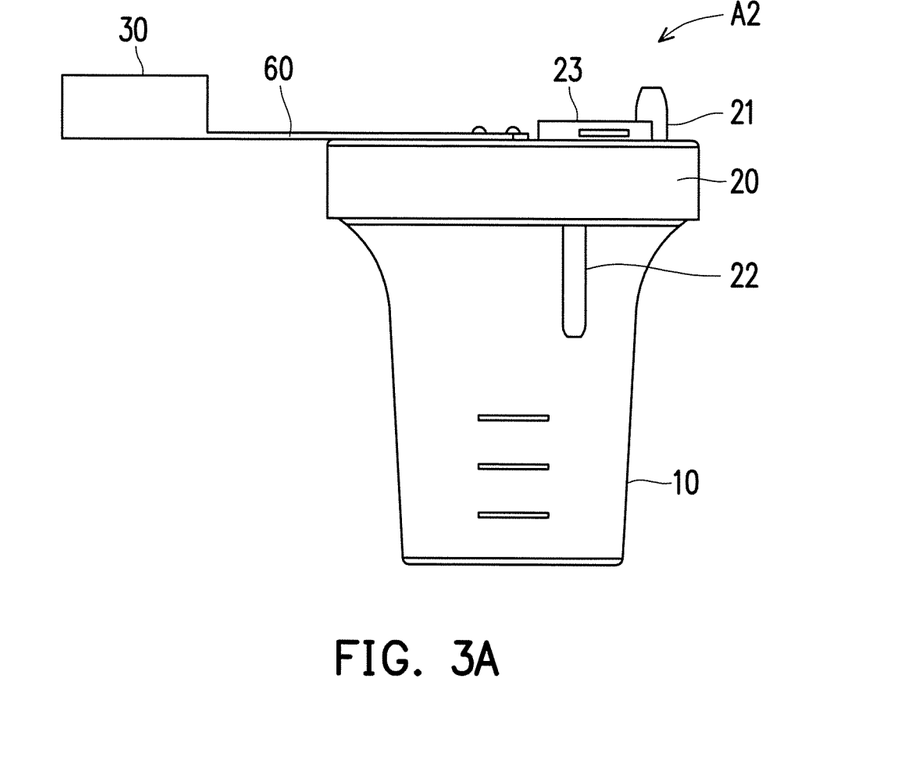
FIG. 3A is a schematic side view illustrating a collection bottle according to another embodiment of the invention.
Figure 3B:
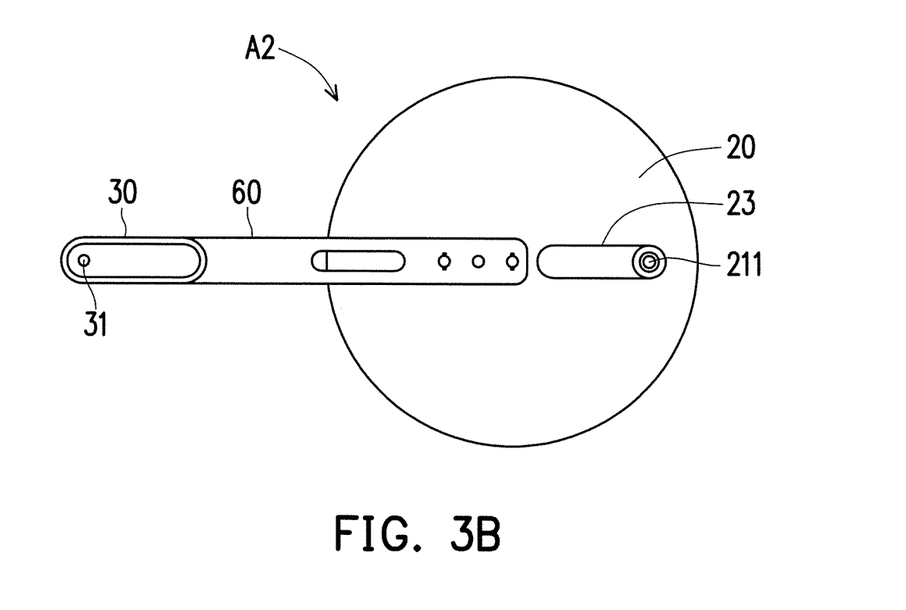
FIG. 3B is a schematic top view illustrating the collection bottle of FIG. 3A.
Figure 3C:
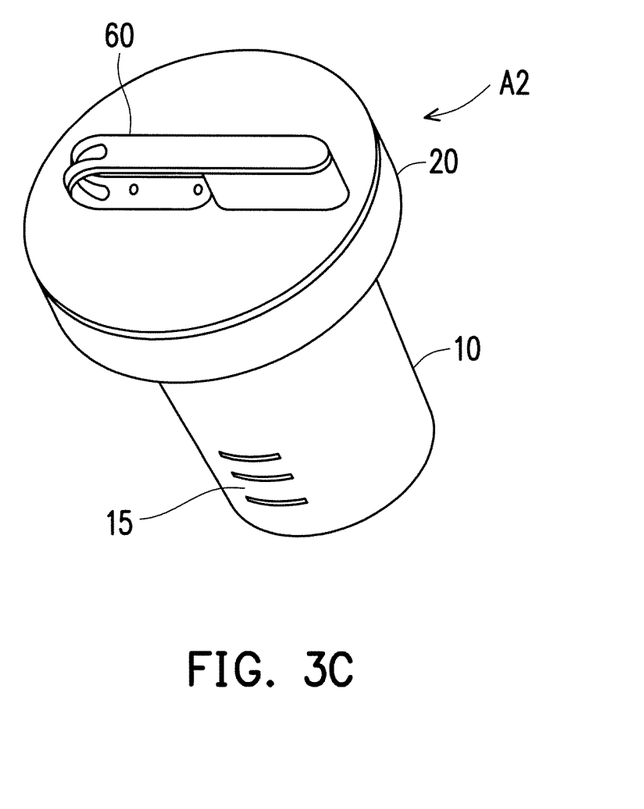
FIG. 3C is a schematic perspective view illustrating the collection bottle of FIG. 3A.

As shown in FIGS. 3A to 3C, the shielding cap 30 of the collection bottle A2 of the embodiment can optionally include an extended connection band 60. An end of the connection band is connected to the cover 20. The connection band 60 used to connect the cover 20 and the shielding cap 30 to prevent the shielding cap 30 from being lost due to inappropriate storage after the shielding cap 30 is removed from the cover 20. Therefore, it is unnecessary to store the shielding cap 30.

As shown in FIG. 3B, the channel 21 has an export hole 211, and the shielding cap 30 has a sealing member 31. The sealing member 31 can be correspondingly fit into the export hole 211 to prevent the sample 40 from being spilled via the export hole 211 when the shielding cap 30 is assembled onto the cover 20.

Figure 4A:
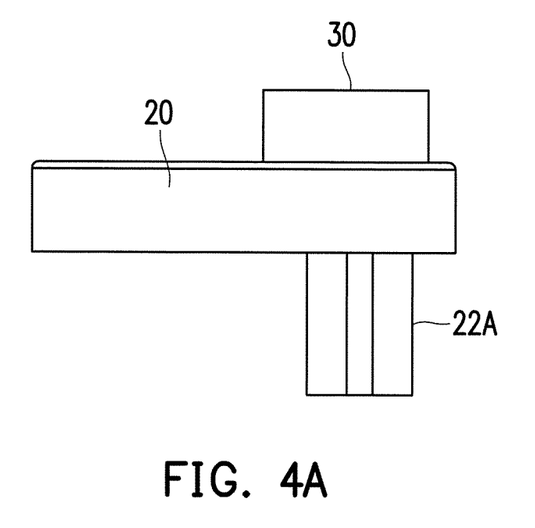
FIG. 4A is a schematic side view illustrating a cover of a collection bottle according to yet another embodiment of the invention.
Figure 4B:
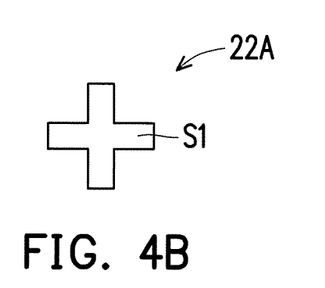
FIG. 4B is a schematic bottom view illustrating a testing part of FIG. 4A.
Figure 4C:
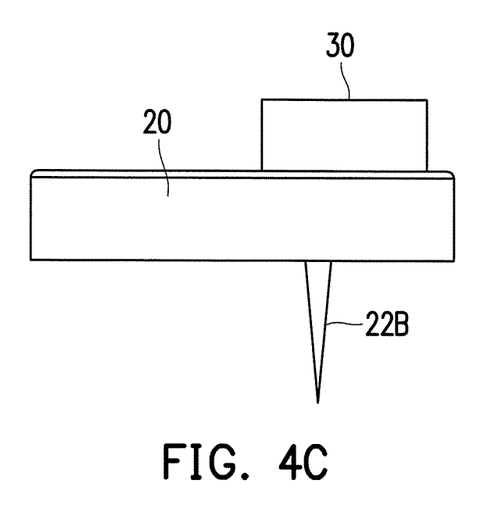
FIG. 4C is a schematic side view illustrating a cover of a collection bottle according to still another embodiment of the invention.
Figure 4D:
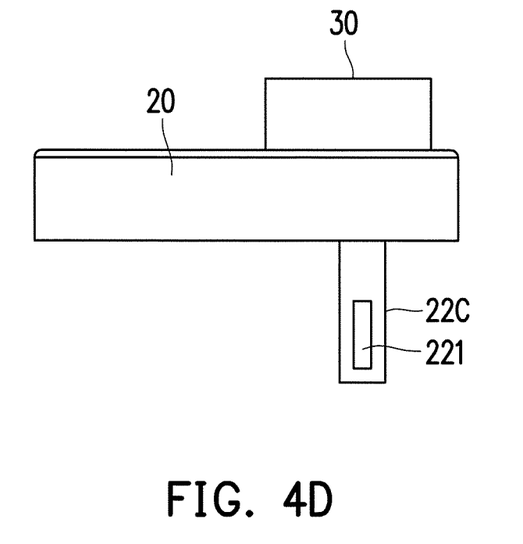
FIG. 4D is a schematic side view illustrating a cover of a collection bottle according to one further embodiment of the invention.
Figure 4E:
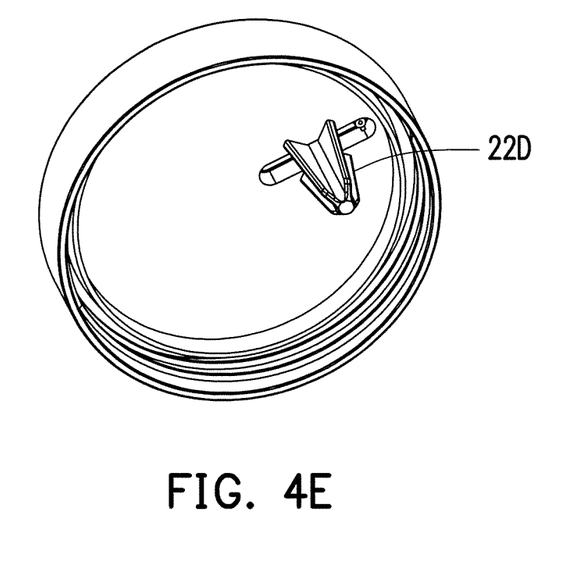
FIG. 4E is a schematic perspective view illustrating a cover of a collection bottle according to another further embodiment of the invention.

As shown in FIGS. 4A and 4B, a testing part 22A of a collection bottle of this embodiment is a cruciform structure formed by a horizontal part and a vertical part. The testing part 22A is disposed to the bottom surface of the cover 20, and a bottom part of the testing part 22A has a bottom surface Si in a cruciform shape to increase an area for the testing part 22A to be dipped in the sample 40. As shown in FIG. 4C, a testing part 22B is a cone-shaped structure with a wider upper section and a narrower lower section, and is disposed to the bottom part of the cover 20. In addition, an end of the testing part 22B extends toward the accommodating space 14. Furthermore, as shown in FIG. 4D, a testing part 22C is a column-shaped structure. The structure has a slot 221 to increase a contact area for dipping in the sample 40. The slot 221 can be a rectangular hollow hole. As shown in FIG. 4E, like the testing part 22A in FIG. 4A, a testing part 22D is cruciform, but is designed to have a gradually reduced size toward the bottom part. As shown the above, the testing part of the invention can exhibit different shapes to fulfill the needs of different tests. For example, the column-shaped structure, the cone-shaped structure, the cruciform structure, or other types of structures can be chosen for the testing part.

Figure 5A:
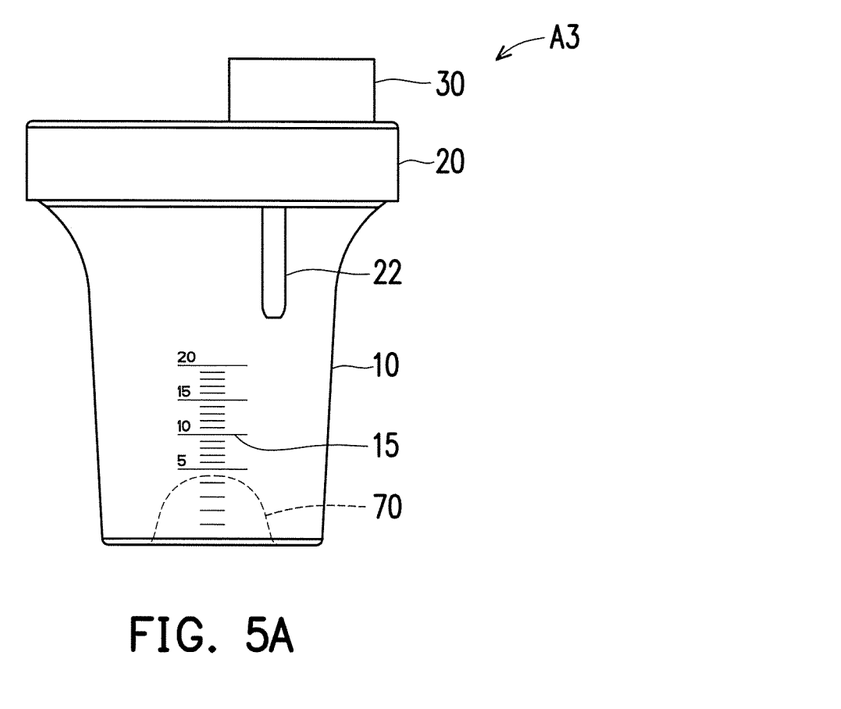
FIG. 5A is a schematic perspective view illustrating a collection bottle according to another embodiment of the disclosure.
Figure 5B:
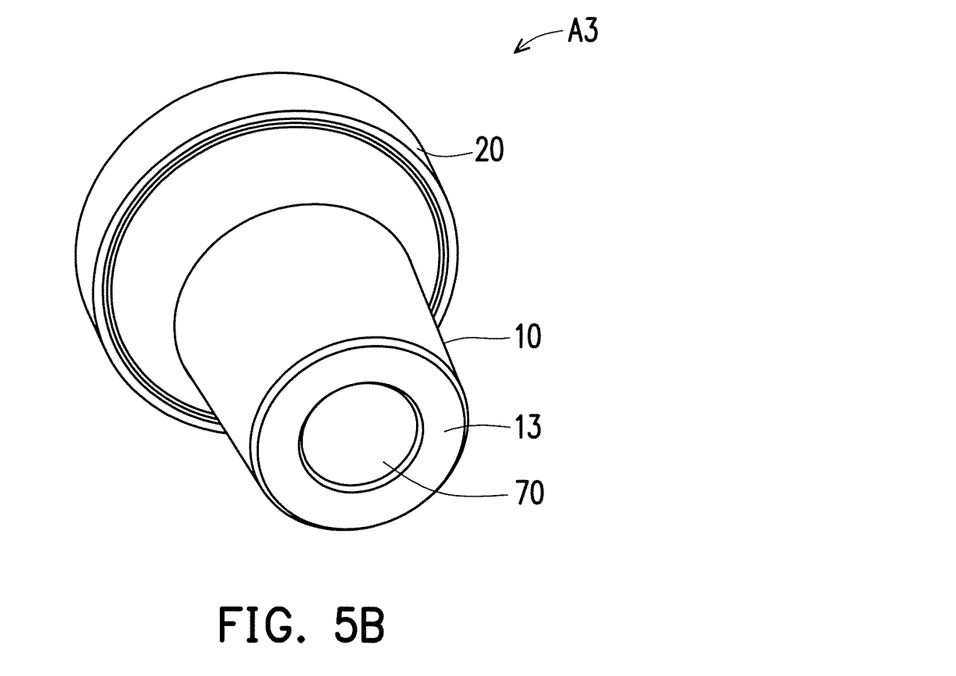
FIG. 5B is a schematic bottom view illustrating the collection bottle of FIG. 5A.

As shown in FIGS. 5A and 5B, a bottom part of the body 10 of a collection bottle A3 of this embodiment has a bulging part 70. The bulging part 70 bulges toward the accommodating space 14, so that a volume of a lower part of the accommodating space 14 is reduced. Therefore, the scale 15 provided on a portion of the body 10 having a height the same with the bulging part 70 can have a greater interval, as shown in FIG. 5A. With the design of the bulging part 70, when the volume of the sample 40 is smaller, the user is able to clearly observe the volume of the sample 40.

In view of the foregoing, the collection bottle according to the embodiments of the invention mainly adopts a novel structural configuration and technical feature with respect to the testing part and the channel. Accordingly, compared with the conventional structure, the characteristic of the sample is able to be detected without opening the cover. In addition, if the sample needs to be taken out, the sample can be exported via the channel on the cover without completely opening the cover. Accordingly, the collection bottle according to the embodiments of the invention allows the user to observe and store the sample more conveniently.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A collection bottle, comprising:
a body, having an accommodating space and a bottom part of said body having a bulging part bulging toward said accommodating space; and
a cover, removably assembled to said body, wherein said cover comprises a channel and a testing part, said channel provides communication between said accommodating space and an outside environment, and said testing part protrudes from a bottom surface of said cover toward said accommodating space and disposed adjacent to said channel,
wherein when said cover is assembled to said body, a fixed distance is capable of being kept between a bottom part of said testing part and said bottom part of said body, and that the collection bottle is capable of being used for the intended use of detecting a dripping state of a sample, said fixed distance being one of the values in a range from 1 mm to 50 mm, and the whole of said testing part is away from said body,
wherein said channel has a portion having an export hole, and wherein said portion of said channel protrudes toward the outside environment and away from said testing part,
wherein a top end of said body has a first width, said bottom part of said body has a second width, and said first width is larger than said second width, and
wherein said body comprises a scale, and a distance between intervals adjacent to each other of said scale below a height of said bulging part is larger than a distance between intervals adjacent to each other of said scale above said height of said bulging part in said accommodating space.

2. The collection bottle as claimed in claim 1, wherein said testing part is a column-shaped structure having a slot, a cone-shaped structure or a cruciform structure.

3. The collection bottle as claimed in claim 2, wherein said testing part is the cruciform structure and is formed by a horizontal part and a vertical part, said testing part being disposed to the bottom surface of said cover and said testing part having a bottom surface in a cruciform shape.

4. The collection bottle as claimed in claim 1, further comprising a test paper or a test reagent disposed on said testing part.

5. The collection bottle as claimed in claim 1, wherein said fixed distance, which is capable of being kept between said bottom part of said testing part and said bottom part of said body is 20 mm.

6. The collection bottle as claimed in claim 1, wherein a material of said body comprises an elastic material.

7. The collection bottle as claimed in claim 1, further comprising a shielding cap removably assembled to said cover and configured to close said channel.

8. The collection bottle as claimed in claim 7, wherein said shielding cap has an extended connection band, and an end of said connection band is connected to said cover.

9. The collection bottle as claimed in claim 7, wherein said cover further comprises a fixing part located adjacent to said channel, and said shielding cap is configured to be engaged with said fixing part and close said channel.

10. The collection bottle as claimed in claim 1, wherein said testing part is non-overlapping with said channel along a protrusion direction of said channel.

11. The collection bottle as claimed in claim 1, wherein said portion of said channel protrudes from a top surface of said cover toward the outside environment and away from said testing part, and wherein said cover further comprises a fixing part located adjacent to said channel, and said fixing part is disposed on and in physical contact with said top surface of said cover.

12. A method for detecting a characteristic of a sample, performed by using said collection bottle as claimed in claim 1, said method comprising: after said cover is opened, placing a sample in said accommodating space, then assembling said cover to said body, and having said testing part dipped in said sample by tilting or shaking, so as to determine said characteristic of said sample.

13. The method as claimed in claim 12, wherein said step of having said testing part dipped in said sample is after an incubation period, and a dripping frequency or a length of stringiness of said sample is observed, so as to determine a level of liquefaction of said sample.

14. The method as claimed in claim 12, wherein after said step of having said testing part dipped in said sample, a test paper or a test reagent disposed on said testing part is observed, so as to detect a characteristic of said sample.

\* \* \* \* \*